(12) United States Patent
Hamada et al.

(10) Patent No.: US 12,252,631 B2
(45) Date of Patent: Mar. 18, 2025

(54) ENDOSCOPIC COATING COMPOSITION, ENDOSCOPIC LUBRICATING MEMBER, METHOD FOR PRODUCING ENDOSCOPIC LUBRICATING MEMBER, ENDOSCOPIC FLEXIBLE TUBE, AND ENDOSCOPE

(71) Applicant: FUJIFILM Corporation, Tokyo (JP)

(72) Inventors: Kazuhiro Hamada, Kanagawa (JP); Yoshihiro Nakai, Kanagawa (JP); Masatoshi Oku, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 733 days.

(21) Appl. No.: 17/517,783

(22) Filed: Nov. 3, 2021

(65) Prior Publication Data
US 2022/0054717 A1    Feb. 24, 2022

Related U.S. Application Data

(63) Continuation of application No. PCT/JP2020/020834, filed on May 27, 2020.

(30) Foreign Application Priority Data

Jun. 13, 2019    (JP) .................................. 2019-110023

(51) Int. Cl.
*C09D 7/45*  (2018.01)
*A61B 1/005* (2006.01)
(Continued)

(52) U.S. Cl.
CPC .............. *C09D 7/45* (2018.01); *A61L 29/085* (2013.01); *A61L 29/10* (2013.01); *A61L 29/14* (2013.01); *C09D 7/61* (2018.01); *C09D 7/69* (2018.01); *C09D 179/08* (2013.01); *A61B 1/005* (2013.01); *A61L 2400/10* (2013.01)

(58) Field of Classification Search
CPC ........ A61L 29/085; A61L 29/10; A61L 29/14; A61L 2400/10; C09D 7/61; C09D 7/69; C09D 179/08; A61B 1/005
See application file for complete search history.

(56) References Cited

U.S. PATENT DOCUMENTS

| | | | |
|---|---|---|---|
| 2011/0305872 | A1 | 12/2011 | Li et al. |
| 2013/0084460 | A1 | 4/2013 | Xu et al. |
| 2013/0131450 | A1 | 5/2013 | Surti et al. |

(Continued)

FOREIGN PATENT DOCUMENTS

| | | |
|---|---|---|
| CN | 103037913 A | 4/2013 |
| CN | 103180352 A | 6/2013 |

(Continued)

OTHER PUBLICATIONS

Communication dated Apr. 1, 2022 from the Chinese Patent Office in corresponding Chinese Application No. 202080031566.4.

(Continued)

*Primary Examiner* — Michael C Miggins
(74) *Attorney, Agent, or Firm* — Sughrue Mion, PLLC (57) ABSTRACT

An endoscopic coating composition including a solid lubricant, a fluorine-containing surfactant, a thermosetting resin, and a solvent, a lubricating member provided by a coating treatment using the coating composition and being suitable as an endoscopic member, a method for producing the lubricating member, and an endoscopic flexible tube and an endoscope including the lubricating member.

20 Claims, 2 Drawing Sheets

(51) Int. Cl.
*A61L 29/08* (2006.01)
*A61L 29/10* (2006.01)
*A61L 29/14* (2006.01)
*C09D 7/40* (2018.01)
*C09D 7/61* (2018.01)
*C09D 179/08* (2006.01)

(56) References Cited

U.S. PATENT DOCUMENTS

2016/0115421 A1 4/2016 Sasaki et al.
2019/0059700 A1 2/2019 Matsuda

FOREIGN PATENT DOCUMENTS

| CN | 105324448 A | 2/2016 |
|---|---|---|
| CN | 208926521 U | 6/2019 |
| JP | 62-134616 A | 6/1987 |
| JP | 7-155281 A | 6/1995 |
| JP | 7-171092 A | 7/1995 |
| JP | 2004-208962 A | 7/2004 |
| JP | 2009-180 A | 1/2009 |
| WO | 2018/034021 A1 | 2/2018 |

OTHER PUBLICATIONS

International Search Report dated Sep. 1, 2020 in International Application No. PCT/JP2020/020834.
Written Opinion of the International Searching Authority dated Sep. 1, 2020 in International Application No. PCT/JP2020/020834.
International Preliminary Report on Patentability dated Dec. 14, 2021 with a translation of the Written Opinion in International Application No. PCT/JP2020/020834.
Extended European Search Report dated Jul. 8, 2022 in European Application No. 20822810.6.

FIG. 1

FIG. 2

ENDOSCOPIC COATING COMPOSITION, ENDOSCOPIC LUBRICATING MEMBER, METHOD FOR PRODUCING ENDOSCOPIC LUBRICATING MEMBER, ENDOSCOPIC FLEXIBLE TUBE, AND ENDOSCOPE

CROSS-REFERENCE TO RELATED APPLICATIONS

This application is a Continuation of PCT International Application No. PCT/JP2020/020834 filed on May 27, 2020, which claims priority under 35 U.S.C. § 119 (a) to Japanese Patent Application No. 2019-110023 filed in Japan on Jun. 13, 2019. Each of the above applications is hereby expressly incorporated by reference, in its entirety, into the present application.

BACKGROUND OF THE INVENTION

1. Field of the Invention

The present invention relates to an endoscopic coating agent, an endoscopic lubricating member, a method for producing an endoscopic lubricating member, an endoscopic flexible tube, and an endoscope.

2. Description of the Related Art

The endoscope is a medical device that is used for observation within the body cavity of a patient, and may include treatment tools such that various treatments can be performed with the endoscope inserted into the body cavity.

The endoscope includes, on the distal-end side of the insertion part, a bending part that is bendable so as to change the direction of the field of observation view to the desired direction. For this bending part, for example, a wire that is a stranded bundle of wires of a metal such as stainless steel is inserted through the endoscope insertion part; the operating unit at the proximal end is controlled to pull the wire to thereby bend the bending part in the desired direction. This wire is inserted through the wire guide disposed on the inner wall of the endoscope insertion part, and fixed so as to be slidable along the inner wall of the endoscope insertion part. The operation itself of the bending part using the wire is a function included in ordinary endoscopes, and is disclosed in, for example, WO2018/034021A and JP2009-180A. For the ordinary configurations of the wire and the wire guide in the bending part, reference can be made to FIG. 2 in WO2018/034021A and FIG. 6 in JP2009-180A, for example.

The bending operation of the bending part causes friction between the wire and the wire guide, and the resultant wear of the wire becomes problematic. In order to reduce the wear, the surface of the wire is ordinarily subjected to a coating treatment using a solid lubricant composed of inorganic particles or organic particles (for example, JP2004-208962A).

The coating treatment using a solid lubricant is ordinarily performed by preparing a coating composition (coating agent) in which the solid lubricant is dispersed in a medium, and applying the coating composition, by, for example, spraying, to the surface of the member to be coated. This coating composition includes, as the medium, a solvent and ordinarily, as a binder, a resin. In addition to the coating by application, JP1995-155281A (JP-H7-155281A) discloses a method of treating the surface of a polymer-material member to be coated, with a solvent that dissolves the member to be coated, to achieve bonding between and joining of a solid lubricant and the surface of the member to be coated.

SUMMARY OF THE INVENTION

In such a case of performing coating with a solid lubricant using a coating composition prepared by dispersing the solid lubricant in a medium, the coating composition needs to have dispersion stability of the solid lubricant particles. Thus, the coating composition ordinarily includes a dispersing agent for improving the dispersibility of the solid lubricant. The dispersing agent is a compound having both of a group that adsorbs onto the solid lubricant (for example, an active hydrogen-containing group such as a carboxy group) and a moiety having an affinity for the solvent.

When the coated member in which the coating layer including the solid lubricant is formed is an endoscopic member represented by the above-described wire, the coating layer needs to sufficiently maintain the covering state of the coating layer (have flux resistance) even in the case of contact with a flux used in solder-bonding. For example, the wire for controlling bending of the endoscope bending part is subjected to a coating treatment using a solid lubricant, and its tip part is solder-bonded to the bending part of the flexible tube. Before the solder-bonding is performed, the bonding portion is coated with a flux in advance. This flux is an agent ordinarily used for solder-bonding, and having functions of lowering the surface tension to facilitate spreading of the solder and preventing oxidation of the bonding portion, to thereby improve bondability of the solder. The inventors of the present invention performed studies and have found the following: upon contact of this flux with the coating layer including a solid lubricant, for example, the flux permeates the coating layer, to cause, from the portion of the contact as the starting point, separation of the coating layer.

An object of the present invention is to provide an endoscopic coating composition that has high dispersion stability of a solid lubricant, that is applied to the surface of an endoscopic member to form a coating layer, to thereby impart high lubricity to the endoscopic member, that maintains this lubricity during repeated use of the endoscope for a long term, and that provides sufficiently high flux resistance of the coating layer. Another object of the present invention is to provide an endoscopic lubricating member provided by a coating treatment using the coating composition and a method for producing the endoscopic lubricating member. Still another object of the present invention is to provide an endoscopic flexible tube and an endoscope that include the endoscopic lubricating member.

In order to achieve the above-described objects, the inventors of the present invention performed thorough studies. As a result, they have found the following: during preparation of a coating composition in which a solid lubricant is dispersed in a solvent, a fluorine-containing surfactant (fluorosurfactant) is added and, as a binder, a thermosetting resin is further added, so that a coated member provided by a coating treatment using this composition has high wear durability and maintains high lubricity for a long term even under repeated friction, and the coated member, upon contact with a flux, is less likely to undergo separation of the coating layer. In addition, in this composition, the fluorine-containing surfactant also effectively functions as a dispersing agent for the solid lubricant, to provide sufficiently improved dispersion stability of the composition without addition of another dispersing agent. On the basis of these findings, they performed further studies, to accomplish the present invention.

The above-described objects of the present invention have been achieved by the following means.

[1]

An endoscopic coating composition including a solid lubricant, a fluorine-containing surfactant, a thermosetting resin, and a solvent.

[2]

The endoscopic coating composition according to [1], wherein the fluorine-containing surfactant includes a nonionic fluorine-containing surfactant.

[3]

The endoscopic coating composition according to [1] or [2], wherein the fluorine-containing surfactant includes a fluorine-containing surfactant having at least one moiety of an alcoholic hydroxy group, a polyether structure, or a (meth)acrylate monomer-derived component.

[4]

The endoscopic coating composition according to any one of [1] to [3], wherein the fluorine-containing surfactant includes a fluorine-containing surfactant having a polyoxyalkylene structure.

[5]

The endoscopic coating composition according to any one of [1] to [4], wherein the thermosetting resin includes a polyamide-imide resin.

[6]

The endoscopic coating composition according to [5], wherein the polyamide-imide resin includes, as a polyamide-imide constituent component, a structural unit represented by Formula (1) below:

Formula (1)

where Ar represents a divalent group having an aromatic ring.

[7]

The endoscopic coating composition according to [6], wherein Ar in Formula (1) above represents phenylene, a diphenylmethane structure, a diphenylpropane structure, a diphenyl ether structure, a diphenyl sulfone structure, a diphenylamine structure, a biphenyl structure, or a naphthalene structure.

[8]

The endoscopic coating composition according to [7], wherein Ar in Formula (1) above represents phenylene, a diphenylmethane structure, a diphenylpropane structure, a diphenyl ether structure, or a diphenylamine structure.

[9]

The endoscopic coating composition according to any one of [5] to [8], wherein the polyamide-imide resin has a weight-average molecular weight of 10000 to 100000.

[10]

The endoscopic coating composition according to any one of [1] to [9], wherein the solid lubricant includes inorganic particles, and the inorganic particles include at least one of graphite, graphite fluoride, carbon nanotubes, boron nitride, molybdenum disulfide, organic molybdenum, or tungsten disulfide.

[11]

The endoscopic coating composition according to [10], wherein the inorganic particles have a particle size of 0.2 to 4.0 μm.

[12]

The endoscopic coating composition according to [11], wherein the inorganic particles have a particle size of 0.3 to 1.5 μm.

[13]

The endoscopic coating composition according to any one of [1] to [12], wherein the solid lubricant includes organic particles, and the organic particles include at least one of a fluororesin or melamine cyanurate.

[14]

The endoscopic coating composition according to [13], wherein the organic particles have a particle size of 0.5 to 30 m.

[15]

The endoscopic coating composition according to [14], wherein the organic particles have a particle size of 1 to 15 μm.

[16]

The endoscopic coating composition according to any one of [1] to [15], wherein the solvent includes at least one of N-methyl 2-pyrrolidone, xylene, N,N-dimethylacetamide, N,N-dimethylformamide, hexamethylphosphoric triamide, or 1,3-dimethyl-2-imidazolidinone.

[17]

An endoscopic lubricating member provided by a coating treatment using the endoscopic coating composition according to any one of [1] to [16].

[18]

The endoscopic lubricating member according to [17], wherein the endoscopic lubricating member is an endoscopic lubricating wire.

[19]

A method for producing an endoscopic lubricating member, the method including coating a surface of an endoscopic member with the endoscopic coating composition according to any one of [1] to [16].

[20]

An endoscopic flexible tube including the endoscopic lubricating member according to [17] or [18].

[21]

An endoscope including the endoscopic flexible tube according to [20].

In this Specification, structures that are not described as to whether or not the structures are substituted or unsubstituted mean that the structures may have optional substituents as long as desired advantages are provided.

In this Specification, "a value 'to' another value" used is intended to include the value and the other value respectively as the lower-limit value and the upper-limit value.

An endoscopic coating composition according to the present invention has high dispersion stability of the solid lubricant, is applied to the surface of an endoscopic member to form a coating layer, to thereby impart high lubricity to the endoscopic member, sufficiently maintains this lubricity for a long term even during repeated use of the endoscope, and also provides sufficiently improved flux resistance of the coating layer. An endoscopic lubricating member according to the present invention has high wear durability, exhibits lubricity for a long term, and also has high flux resistance. A method for producing an endoscopic lubricating member according to the present invention provides an endoscopic lubricating member that has high wear durability, exhibits lubricity for a long term, and also has high flux resistance. An endoscopic flexible tube and an endoscope according to the present invention include an endoscopic lubricating member according to the present invention; this lubricating member has high wear durability, maintains its lubricity for a long term even during repeated use of the endoscope, and also has high flux resistance. Therefore, an endoscopic flexible tube and an endoscope according to the present invention have high operation durability.

DESCRIPTION OF THE PREFERRED EMBODIMENTS

Endoscopic Coating Composition

An endoscopic coating composition according to the present invention (hereafter, also referred to as a composition according to the present invention) contains a solid lubricant, a fluorine-containing surfactant, a thermosetting resin, and a solvent.

Solid Lubricant

For the solid lubricant included in a composition according to the present invention, wide-ranging solid lubricants ordinarily used are applicable. Thus, the solid lubricant used in the present invention may be inorganic particles, organic particles, or a combination of these. For the solid lubricant, "solid" means being in the form of solid at 25° C.

Examples of the material of the solid lubricant composed of inorganic particles include graphite, graphite fluoride, carbon nanotubes, boron nitride, molybdenum disulfide, organic molybdenum, and tungsten disulfide; these may be used alone or in combination of two or more thereof. Note that, in the present invention, "organic molybdenum", which is a solid lubricant that mainly contains molybdenum, is classified as inorganic particles for convenience.

When the solid lubricant is inorganic particles, the inorganic particles may have a particle size of, for example, 0.2 to 6.0 μm, preferably 0.2 to 4.0 μm, more preferably 0.2 to 3.5 μm, still more preferably 0.3 to 2.0 μm, still more preferably 0.3 to 1.5 μm, particularly preferably 0.35 to 1.3 μm. In the present invention and Specification, the particle size means volume-average particle size.

Examples of the material of the solid lubricant composed of organic particles include fluororesins and melamine cyanurate ("melamine cyanurate" is intended to include its tautomer, melamine isocyanurate). Examples of the fluororesins include polytetrafluoroethylene (PTFE), polychlorotrifluoroethylene (PCTFE), polyvinylidene fluoride (PVDF), and polyvinyl fluoride (PVF); of these, PTFE is preferred.

When the solid lubricant is organic particles, the organic particles may have a particle size of 0.5 to 30 μm or 1 to 30 μm, preferably 1 to 25 μm, more preferably 1 to 20 μm, still more preferably 1 to 15 μm, still more preferably 1.5 to 12 μm, still more preferably 2 to 10 μm, particularly preferably 2 to 8 μm.

A composition according to the present invention preferably includes, as the solid lubricant, at least inorganic particles. When a composition according to the present invention contains, as the solid lubricant, inorganic particles and organic particles, the mass content ratio of these two particle species is preferably [inorganic particles]/[organic particles]≥0.3, more preferably [inorganic particles]/[organic particles]≥0.5, preferably [inorganic particles]/[organic particles]≥1, preferably [inorganic particles]/[organic particles]≥1.5, preferably [inorganic particles]/[organic particles]≥1.7.

In a composition according to the present invention, the content of the solid lubricant is preferably 5 to 60 mass %, more preferably 10 to 50 mass %, more preferably 15 to 45 mass %, still more preferably 25 to 40 mass %, particularly preferably 26 to 35 mass %.

Fluorine-Containing Surfactant

As the fluorine-containing surfactant (fluorosurfactant), wide-ranging known fluorine-containing surfactants are usable. Examples include nonionic fluorine-containing surfactants, anionic fluorine-containing surfactants, amphoteric fluorine-containing surfactants, and oligomer-type fluorine-containing surfactants. For the fluorine-containing surfactant, the number of carbon atoms to which fluorine atoms are bonded in a single molecule (the number of fluorine-substituted carbon atoms) is preferably 2 to 16, and more preferably the number of fluorine-substituted carbon atoms is 2 to 8. Such a fluorine-substituted carbon atom is preferably present as a perfluoroalkyl group or a perfluoroalkenyl group. In other words, a fluorine-containing surfactant according to the present invention preferably has a perfluoroalkyl group and/or a perfluoroalkenyl group.

Examples of the nonionic fluorine-containing surfactants include perfluoroalkyl phosphate compounds, perfluoroalkylethylene oxide adducts, perfluoroalkylpropylene oxide adducts, and polyoxyalkylene ether polymer compounds having a perfluoroalkyl ether group in a side chain.

Examples of the anionic fluorine-containing surfactants include perfluoroalkylsulfonic acid compounds, perfluoroalkylcarboxylic acid compounds, perfluoroalkylphosphate compounds, and polyoxyalkylene ether polymer compounds having a perfluoroalkyl ether group in a side chain.

Examples of the amphoteric fluorine-containing surfactants include perfluoroalkylbetaine.

Examples of the perfluoroalkylsulfonic acid compounds include perfluoroalkylsulfonic acids and perfluoroalkylsulfonic acid salts.

Examples of the perfluoroalkylcarboxylic acid compounds include perfluoroalkylcarboxylic acids and perfluoroalkylcarboxylic acid salts.

Examples of the perfluoroalkylphosphate compounds include (nonionic) perfluoroalkylphosphates having a structure in which the hydrogen atoms of all —OHs of the phosphoric acid are substituted with perfluoroalkyl groups, and (anionic) perfluoroalkylphosphates having a structure in which the hydrogen atoms of one or more —OHs of the phosphoric acid are substituted with perfluoroalkyl groups or (anionic) salts thereof.

Examples of the polyoxyalkylene ether polymer compounds having a perfluoroalkyl ether group in a side chain include (nonionic) polyoxyalkylene ether polymers having a perfluoroalkyl ether group in a side chain, and (anionic) polyoxyalkylene ether polymer salts having a perfluoroalkyl ether group in a side chain (such as sulfate salts).

When the anionic fluorine-containing surfactants have the form of salt, examples of the counter ions include alkali metal ions and ammonium ions; specific examples include cations such as Li, Na, K, $NH_4$, $NH_3CH_2CH_2OH$, $NH_2(CH_2CH_2OH)_2$, and $NH(CH_2CH_2OH)_3$.

A composition according to the present invention preferably includes, as the fluorine-containing surfactant, at least a nonionic fluorine-containing surfactant. The fluorine-containing surfactant included in a composition according to the present invention is preferably a nonionic fluorine-containing surfactant.

A composition according to the present invention preferably includes, as the fluorine-containing surfactant, a fluorine-containing surfactant having, in the molecule, at least one moiety of an alcoholic hydroxy group, a polyether structure, or a (meth)acrylate monomer-derived component. In particular, as the fluorine-containing surfactant, a fluorine-containing surfactant having a polyether structure is preferably included.

A composition according to the present invention preferably includes, as the fluorine-containing surfactant, a fluorine-containing surfactant having, in the molecule, a polyoxyalkylene structure (structure having 2 or more (for example, 2 to 50, preferably 2 to 20) oxyalkylene repeating units). For each of the alkylene groups constituting the polyoxyalkylene structure, the number of carbon atoms is preferably an integer of 1 to 10, more preferably 1 to 6, still more preferably 2 or 3. The polyoxyalkylene structure is more preferably a polyoxyethylene structure. The fluorine-containing surfactant included in a composition according to the present invention is also preferably a fluorine-containing surfactant having, in the molecule, a polyoxyalkylene structure.

The fluorine-containing surfactant contributes to stabilization of the surface treatment state of the coated member having a surface subjected to a coating treatment using a composition according to the present invention. For example, the fluorine-containing surfactant improves durability against a flux used in a large amount during solder-bonding.

In general, in the case of forming, on the surface of, for example, the operating wire of an endoscope, a coating layer including a solid lubricant, during solder-bonding of the tip portion of the wire and the wall surface of the endoscope flexible tube, the adhesiveness between the coating layer in contact with a flux and the wire surface tends to lower. This lowering of the adhesiveness causes separation of the coating layer; this separation spreads with time to the area surrounding the portion in contact with the flux, which leads to degradation of wear durability of the wire. This is caused inferentially because, for example, the flux permeates, through the surface of the coating layer, the coating layer.

However, in the case of forming this coating layer so as to include a fluorine-containing surfactant, separation of the coating layer even in the case of contact with a flux is sufficiently suppressed. The reason for this is not clarified, but is inferred that the fluorine-containing surfactant exerts an action of repelling the flux at the surface of the coating layer or an action of, within the coating layer, blocking permeation of the flux.

In addition, the fluorine-containing surfactant exhibits appropriate compatibility with a thermosetting resin described later, and also contributes to improvement in the wear durability of the resultant coating layer.

In addition, the fluorine-containing surfactant also effectively functions as a dispersing agent for the solid lubricant in a composition according to the present invention. Ibis is inferentially caused because, for example, the fluorine-containing surfactant in the composition reduces the aggregation force of the solid particles. Thus, a composition according to the present invention exhibits, without including another dispersing agent for the solid lubricant, sufficient dispersion stability as a coating composition.

Examples of the commercially available product of the fluorine-containing surfactant include SURFLON 5-111, S-112, S-113, S-121, S-131, S-132, S-141, S-145, S-211, S-221, S-231, S-232, S-233, S-241, S-242, S-243, S-420 (all are manufactured by Asahi Glass Co., Ltd.); FLUORAD FC-93. FC-95, FC-98, FC-129, FC-135, FC-170C. FC-430, FC-431 (all are manufactured by Sumitomo 3M Limited);

MEGAFACE F-114, F-444, F-470, F-1405, F-474, F-251, F-253, F-281, F-410, F-430, F-444, F-477, F-510, F-511, F-551, F-552, F-553, F-554, F-555, F-556, F-557, F-558, F-559, F-560, F-561, F-562, F-563. F-565, F-568, F-569, F-570, F-571, F-572 (all are manufactured by DIC Corporation);

ZONYL TBS, FSP, FSA, FSN-100, FSN, FSO-100, FSO, FS-300, UR (all are manufactured by E. I. du Pont de Nemours and Company);

FTERGENT FT-110, FT-SW100, FT-100C, FT-150, FT-150CH, FT-250, FT-251, FT-212M, FT-215M, FT-250, FT-209F, FT-222F, FT-245F, FT-208G, FT-300, FT-310, FT-320, FT-400S, FT-400SW, FT-150, FT-400, FT-218GL, FT-240G, FT-212P, FT-220P, FT-228P, FTX-218, DFX-18, FT-610FM, FT-710FL, FT-710FM, FT-710FS, FT-730FL, FT-730LM (all are manufactured by NEOS COMPANY LIMITED); and POLYFOX PF-136A, PF-156A. PF-151N, PF-154, PF-159 (all are manufactured by OMNOVA Solutions Inc.).

Other preferred examples of the fluorine-containing surfactant include 2-(perfluorohexyl)ethanol and 2-(perfluorohexyl)hexanol.

In a composition according to the present invention, the content of the fluorine-containing surfactant is preferably 0.1 to 20 mass %, more preferably 0.1 to 15 mass %, still more preferably 0.2 to 10 mass %, still more preferably 0.2 to 8 mass %, still more preferably 0.2 to 5 mass %, still more preferably 0.2 to 3 mass %, particularly preferably 0.3 to 2 mass %.

Thermosetting Resin

A composition according to the present invention contains a thermosetting resin. This thermosetting resin functions as a binder. The use of the thermosetting resin provides high wear durability of a coated member treated with a composition according to the present invention.

The thermosetting resin is not particularly limited. Examples include polyamide-imide resins, polyimide resins (including resins present as polyamic acid in the composition), epoxy resins, phenol resins, melamine resins, and urea resins. In particular, the thermosetting resin preferably includes a polyamide-imide resin, and the thermosetting resin is more preferably a polyamide-imide resin.

The polyamide-imide resin preferably includes, as the polyamide-imide constituent component, a structural unit represented by Formula (1) below.

Formula (1)

In Formula, Ar represents a divalent group having an aromatic ring.

Ar is preferably phenylene, a diphenylmethane structure (-phenylene-$CH_2$-phenylene-), a diphenylpropane structure (-phenylene-$C_3H_6$-phenylene-), a diphenyl ether structure (-phenylene-O-phenylene-), a diphenyl sulfone structure (-phenylene-$SO_2$-phenylene-), a diphenylamine structure (-phenylene-NH-phenylene-), a biphenyl structure (-phenylene-phenylene-), or a naphthalene structure, more preferably phenylene, a diphenylmethane structure, a diphenylpropane structure, a diphenyl ether structure, or a diphenylamine structure.

In the polyamide-imide, the content of the structural unit represented by Formula (1) above is preferably 50 mass % or more, more preferably 70 mass % or more, more preferably 80 mass % or more, still more preferably 90 mass % or more. The polyamide-imide is also preferably composed of the structural unit represented by Formula (1) above.

The polyamide-imide preferably has a weight-average molecular weight of 10000 to 100000.

In a composition according to the present invention, the content of the thermosetting resin is preferably 0.5 to 20 mass %, more preferably 1 to 15 mass %, still more preferably 2 to 10 mass %, particularly preferably 3 to 8 mass %.

In a composition according to the present invention, relative to 100 parts by mass of the content of the solid lubricant, the content of the fluorine-containing surfactant is preferably 0.1 to 50 parts by mass, more preferably 0.2 to 30 parts by mass, still more preferably 0.5 to 20 parts by mass, still more preferably 0.5 to 10 parts by mass, still more preferably 0.7 to 8 parts by mass, particularly preferably 0.8 to 6 parts by mass.

Relative to 100 parts by mass of the content of the solid lubricant, the content of the thermosetting resin is preferably 1 to 50 parts by mass, more preferably 5 to 40 parts by mass, still more preferably 10 to 30 parts by mass, particularly preferably 12 to 25 parts by mass.

In a composition according to the present invention, relative to 100 parts by mass of the content of the thermosetting resin, the content of the fluorine-containing surfactant is preferably 2 to 100 parts by mass, more preferably 3 to 90 parts by mass, still more preferably 4 to 80 parts by mass, still more preferably 5 to 70 parts by mass, still more preferably 5 to 60 parts by mass, still more preferably 6 to 50 parts by mass, particularly preferably 7 to 40 parts by mass.

Solvent

A composition according to the present invention contains, as the dispersion medium for the solid lubricant, a solvent. This solvent is not particularly limited as long as it functions as the dispersion medium. The solvent is preferably an organic solvent.

Examples of the solvent usable for a composition according to the present invention include N-methyl-2-pyrrolidone (NMP), xylene, N,N-dimethylacetamide, N,N-dimethylformamide, hexamethylphosphoric triamide, and 1,3-dimethyl-2-imidazolidinone. Specifically, as the solvent used in a composition according to the present invention, these solvents are preferably included alone or in combination of two or more thereof.

In a composition according to the present invention, the content of the solvent is not particularly limited as long as the solvent functions as the dispersion medium for the solid lubricant and forms, together with the thermosetting resin, the composition. For example, in the composition, the solvent content may be 10 to 90 mass %, is preferably 20 to 80 mass %, more preferably 40 to 70 mass %.

A composition according to the present invention may appropriately contain, in addition to the above-described components, ordinarily used various additives as long as advantages of the present invention are not degraded. Examples of the additives include plasticizers, coloring agents, defoaming agents, surfactants, and dispersing agents.

Preparation of Endoscopic Coating Composition

A composition according to the present invention can be obtained by homogeneously mixing the above-described components using a homogenizer, for example.

Note that, in the present invention, "composition" is intended to encompass, in addition to a form in which the components are each homogeneously present in the composition, a form in which some components are localized as long as advantages of the present invention are not degraded.

A composition according to the present invention is suitably usable as a coating agent for imparting lubricity to various members (endoscopic members) used for endoscopes. For example, the composition is applicable to the surface of a wire inserted through the endoscope insertion part in order to bend the bending part of the endoscope insertion part in a desired direction. This effectively reduces friction between the wire and the wire guide, to improve wear durability of the wire. The composition is also applicable to the surface of the resin cover layer of an endoscopic flexible tube.

Endoscopic Lubricating Member

An endoscopic lubricating member according to the present invention (hereafter, also referred to as "lubricating member according to the present invention") is an endoscopic member provided by a coating treatment using a composition according to the present invention. The method of performing the coating treatment using a composition according to the present invention is not particularly limited. For example, a composition according to the present invention is applied to the surface of a member to be coated, and subsequently dried to remove the solvent, to thereby achieve coating of the surface of the member to be coated, with a solid lubricant. The coating can be performed by a spraying process, an immersion process, a coating process using a brush or a roller, or a bar coating process, for example.

A lubricating member according to the present invention is preferably an endoscopic lubricating wire. This lubricating wire can be obtained by, as described above, applying a composition according to the present invention to the surface of the wire to be inserted through the endoscope insertion part.

Endoscopic Flexible Tube and Endoscope

Figure 1:
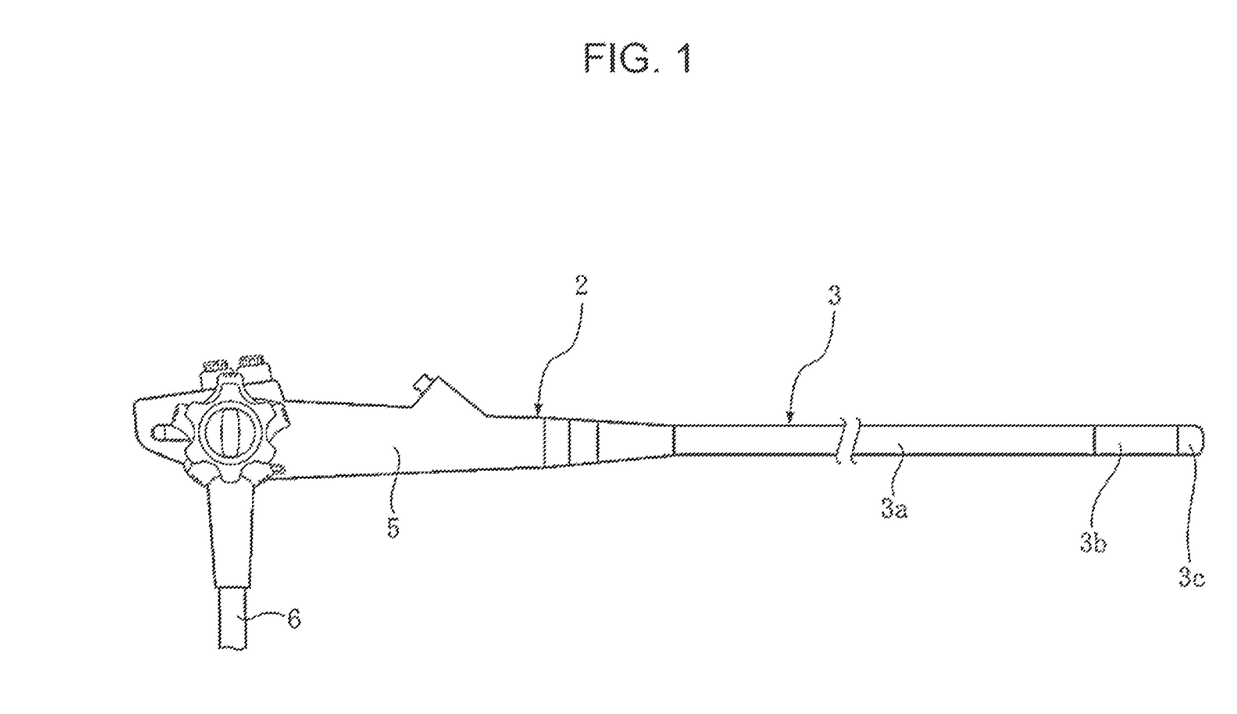
FIG. 1 is an external view illustrating the configuration of an electronic endoscope according to an embodiment.

A preferred embodiment of an endoscope according to the present invention will be described with reference to an electronic endoscope serving as an example. Into the electronic endoscope, an endoscopic flexible tube (hereafter, the endoscopic flexible tube may be simply referred to as "flexible tube") is incorporated, so that the electronic endoscope is used as a medical device for inserting the flexible tube into the body cavity in order to perform, for example, observation within the body cavity. In an example illustrated in FIG. 1, an electronic endoscope 2 includes an insertion part 3 configured to be inserted into the body cavity, a main-body operating unit 5 coupled to a proximal end part of the insertion part 3, and a universal cord 6 connected to a processor device and a light source device. The insertion part 3 is constituted by a flexible tube 3a coupled to the main-body operating unit 5, a bending part 3b (angle part 3b) coupled to the flexible tube 3a, and a tip part 3c coupled to the tip of the bending part 3b and including an imaging device (not shown) for capturing images of the inside of the body cavity. The flexible tube 3a, which accounts for most of the length of the insertion part 3, has flexibility for almost the entire length; in particular, the part inserted into, for example, the body cavity has a structure having higher flexibility. For the bending part 3b, as described above, a wire inserted through the insertion part 3 and fixed, using the wire guide, on the inner wall of the bending part 3b is pulled to thereby achieve bending in a desired direction. As an example of the form using the wire to achieve bending, reference can be made to FIG. 1 of JP2009-180A, for example.

An endoscopic flexible tube according to the present invention includes a lubricating member according to the present invention. Examples of the lubricating member included in an endoscopic flexible tube according to the present invention include, as described above, wires and resin cover layers.

EXAMPLES

Hereinafter, the present invention will be described further in detail with reference to Examples; however, construction of the present invention is not limited to Examples.

Example 1

Preparation Example 1-1: Preparation of Endoscopic Coating Composition

Into the vessel of a homogenizer (manufactured by NIHONSEIKI KAISHA LTD., trade name: ED-7-type AUTO EXCEL HOMOGENIZER, impeller diameter: 45 mm*), 5.5 g (solid content) of a polyamide-imide resin (manufactured by Hitachi Chemical Company. Ltd., trade name: HPC-6000-26, thermosetting resin, weight-average molecular weight: 40000, the polyamide-imide being composed of the structural unit represented by Formula (1) (Ar is a diphenylmethane structure)), 44.0 g of NMP (manufactured by FUJIFILM Wako Pure Chemical Corporation, this NMP including NMP used as a solvent in HPC-6000-26), 20.0 g of p-xylene (manufactured by FUJIFILM Wako Pure Chemical Corporation, this p-xylene including p-xylene used as a solvent in HPC-6000-26), and 0.5 g of a fluorine-containing surfactant (manufactured by DIC Corporation, trade name: MEGAFACE F-444) were placed, and mixed by stirring at 1000 rpm for 5 minutes.

Subsequently, 20.0 g of molybdenum disulfide (manufactured by Daizo Corporation, trade name: C Powder, particle size: 1.2 μm) and 10.0 g of PTFE particles (manufactured by KITAMURA LIMITED, trade name: KTL-8N, particle size: 5.0 μm) were added, and mixed by stirring at 7000 rpm for 30 minutes, to obtain a coating composition of Example 1.

Preparation Example 1-2: Preparation of Endoscopic Lubricating Member (Endoscopic Lubricating Wire)

The whole surface of a stainless steel wire (formed of SUS304, 0.5 mmφ, length: 500 mm) was uniformly subjected to spray coating with the coating composition of Example 1 (Preparation Example 1-1) using a hand gun. Subsequently, the composition was dried by heating in an oven at 230° C. for 60 minutes to form a coating layer, to prepare an endoscopic lubricating wire of Example 1. In this endoscopic lubricating wire, the coating layer was found to have a film thickness of 21 μm. This film thickness was a value determined by measuring film thicknesses at randomly selected five points using a micrometer, and averaging the resultant five measured values.

Examples 2 to 34 and Comparative Examples 1 to 9

Coating compositions of Examples 2 to 34 and Comparative Examples 1 to 9 were obtained as in Preparation Example 1-1 except that the raw materials used were changed as described in Tables below.

Subsequently, these coating compositions were used as in Preparation Example 1-2 to obtain endoscopic lubricating wires of Examples 2 to 34 and Comparative Examples 1 to 9.

Note that the formulation amounts of the raw materials in Tables below except for the formulation amounts of solvents are all solid contents.

Test Example 1: Dispersion Stability Test

For each of Examples and Comparative Examples above, the coating composition was evaluated in terms of dispersion stability. After the coating composition was prepared (specifically, after the above-described solid lubricant was added and subsequently stirring at 700 W rpm for 30 minutes was performed), the dispersion state of the composition after the lapse of 1 hour (dispersion state of the solid lubricant in the solvent) was visually observed, and graded into one of the following evaluation grades to perform evaluation.

Evaluation Grades of Dispersion Stability
  A: the dispersion state is homogeneous.
  B: the dispersion state is relatively inhomogeneous, but suspended matter and precipitation do not occur.
  C: the dispersion state is inhomogeneous and suspended matter or precipitation occurs.

Test Example 2: Flux Resistance Test

For each of Examples and Comparative Examples above, to the whole surface of the endoscopic lubricating wire, a water-soluble flux (manufactured by Cookson Electronics Inc., trade name: WS-600) was applied, and heated using a hot plate at 250° C. for 1 minute. From the hot plate, the wire was removed and cooled, subsequently washed with hot water at 60° C. to remove the flux, and dried at room temperature for 24 hours.

The dried wire was wound in the U-shape around a pulley having a radius of 25 mmφ, and moved back and forth 5 times during which the separated coating layer was collected and its weight (mg) was measured. The relationship between the measured value and the total mass (mg) of the coating was graded into one of evaluation grades below, to perform evaluation of flux resistance.

The wire was wound in the U-shape around the pulley such that a portion of the wire having a length of 78.5 mm ([25 mm×2×3.14]/2) (the portion corresponding to a semicircle in the circumference of the pulley) was in contact with the pulley. In this state, an end of the wire under tension was pulled to rotate the pulley for a half rotation (this rotation direction is defined as X direction). Subsequently, the other end of the wire still under tension was pulled to rotate, in the reverse direction, the pulley for one rotation (this rotation direction is defined as Y direction). This completed the first back-and-forth movement. From this state, similarly, the pulley was rotated for one rotation in X direction, and subsequently the pulley was rotated for one rotation in Y direction. These one rotation in X direction and one rotation in Y direction are collectively defined as one back-and-forth movement: this movement was repeated for four back-and-forth movements to perform, together with the first back-and-forth movement, five back-and-forth movements in total during which the separated coating layer was collected and its weight was measured.

The total coating mass (weight (mg) of the coating layer covering the portion "78.5 mm×3=235.5 mm" coming into contact with the pulley during the five back-and-forth movements) was determined by measuring the masses (mg) of the wire before and after coating, and performing calculation by the following formula.

[Total coating mass (mg)]=([mass of wire on which coating layer is formed (mg)]−[mass of wire on which coating layer is to be formed (mg)])× 235.5 mm/500 mm Evaluation Grades of Flux Resistance
  A: separation of the coating layer is not observed, or the mass of the separated coating layer relative to the total coating mass (100 mass %) is less than 10 mass %.
  B: the mass of the separated coating layer relative to the total coating mass is 10 mass % or more and less than 20 mass %.
  C: the mass of the separated coating layer relative to the total coating mass is 20 mass % or more and less than 30 mass %.
  D: the mass of the separated coating layer relative to the total coating mass is 30 mass % or more.

Test Example 3: Wear Durability Test

Figure 2:
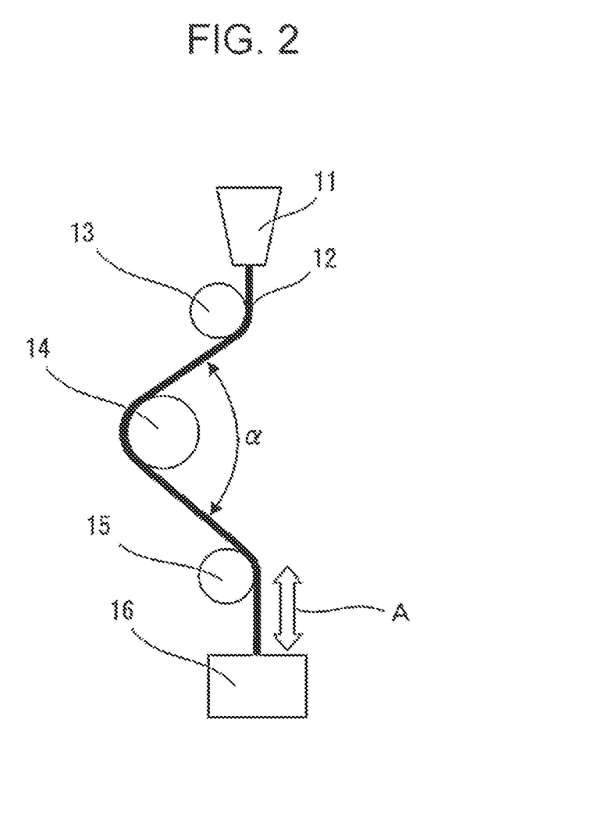
FIG. 2 is an explanatory view illustrating a wear durability test in EXAMPLES.

A test apparatus illustrated in FIG. 2 was used to perform a wear durability test. As illustrated in FIG. 2, an endoscopic lubricating wire (12) obtained in each of Examples and Comparative Preparation Examples above was disposed along a φ5 mm SUS rod (14) and pulleys (13, 15) such that an angle (α) was 100°. A weight (16) was used to apply a load of 10 N: this state was defined as the initial state of the test.

Subsequently, the weight was pulled downward for a stroke (A) of 10 mm at a speed of 100 mm/min, and subsequently returned to the original state. This operation was defined as one back-and-forth movement: during this one back-and-forth movement, a force gage (11) was used to measure the maximum stress (N), which was recorded as the measured value of the load during the one back-and-forth movement.

The back-and-forth movement was repeated 1000 times for the stroke and at the speed, and the initial load (calculated by, during the 1st back-and-forth movement to the 50th back-and-forth movement, averaging the 50 measured values of the force gage and subtracting, from the average value, the value of the force gage at the initial state of the test) and the final load (calculated by, during the 951st back-and-forth movement to the 1000th back-and-forth movement, averaging the 50 measured values of the force gage and subtracting, from the average value, the value of the force gage at the initial state of the test) were determined. The load increase ratio calculated by the following formula was graded into one of the following evaluation grades to perform evaluation.

Load increase ratio (%)=100×Final load (N)/Initial load (N)

Evaluation Grades of Wear Durability
  A: the load increase ratio is less than 120%.
  B: the load increase ratio is 120% or more and less than 150%.
  C: the load increase ratio is 150% or more and less than 200%.
  D: the load increase ratio is 200% or more.

The results of Test Examples above will be described in the following Tables.

| | | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Solid lubricant | Inorganic particles | (A-3) | (A-1) | (A-2) | (A-4) | (A-5) | (A-6) | (A-7) | (A-8) | (A-9) | (A-10) |
| | Particle size (μm) | 1.2 | 0.45 | 0.63 | 3.5 | 5.2 | 1.0 | 1.5 | 0.5 | 2.0 | 2.0 |
| | Formulation amount (mass %) | 20.0 | 20.0 | 20.0 | 20.0 | 20.0 | 20.0 | 20.0 | 20.0 | 20.0 | 20.0 |
| | Organic particles | (B-4) | (B-4) | (B-4) | (B-4) | (B-4) | (B-4) | (B-4) | (B-4) | (B-4) | (B-4) |
| | Particle size (μm) | 5.0 | 5.0 | 5.0 | 5.0 | 5.0 | 5.0 | 5.0 | 5.0 | 5.0 | 5.0 |
| | Formulation amount (mass %) | 10.0 | 10.0 | 10.0 | 10.0 | 10.0 | 10.0 | 10.0 | 10.0 | 10.0 | 10.0 |
| | Surfactant | (C-1) | (C-1) | (C-1) | (C-1) | (C-1) | (C-1) | (C-1) | (C-1) | (C-1) | (C-1) |
| | Formulation amount (mass %) | 0.5 | 0.5 | 0.5 | 0.5 | 0.5 | 0.5 | 0.5 | 0.5 | 0.5 | 0.5 |
| Binder | Thermosetting resin | (D-1) | (D-1) | (D-1) | (D-1) | (D-1) | (D-1) | (D-1) | (D-1) | (D-1) | (D-1) |
| | Formulation amount (mass %) | 5.5 | 5.5 | 5.5 | 5.5 | 5.5 | 5.5 | 5.5 | 5.5 | 5.5 | 5.5 |
| Solvent | Type | NMP | NMP | NMP | NMP | NMP | NMP | NMP | NMP | NMP | NMP |
| | mass % | 44.0 | 44.0 | 44.0 | 44.0 | 44.0 | 44.0 | 44.0 | 44.0 | 44.0 | 44.0 |
| | Type | p-Xylene | p-Xylene | p-Xylene | p-Xylene | p-Xylene | p-Xylene | p-Xylene | p-Xylene | p-Xylene | p-Xylene |
| | mass % | 20.0 | 20.0 | 20.0 | 20.0 | 20.0 | 20.0 | 20.0 | 20.0 | 20.0 | 20.0 |
| Thickness of coating layer (μm) | | 21 | 15 | 17 | 23 | 25 | 21 | 19 | 16 | 23 | 24 |
| Dispersion stability | | A | A | A | A | A | A | A | A | A | A |
| Flux resistance | | A | A | A | A | A | A | A | A | A | A |
| Wear durability | | A | A | A | B | C | A | A | A | B | B |

|  |  | Example 11 | Example 12 | Example 13 | Example 14 | Example 15 | Example 16 | Example 17 | Example 18 | Example 19 | Example 20 |
|---|---|---|---|---|---|---|---|---|---|---|---|
| Solid lubricant | Inorganic particles | (A-3) | (A-3) | (A-3) | (A-3) | (A-3) | (A-3) | (A-3) | (A-3) | (A-3) | (A-3) |
|  | Particle size (μm) | 1.2 | 1.2 | 1.2 | 1.2 | 1.2 | 1.2 | 1.2 | 1.2 | 1.2 | 1.2 |
|  | Formulation amount (mass %) | 20.0 | 20.0 | 20.0 | 20.0 | 20.0 | 20.0 | 20.0 | 20.0 | 20.0 | 20.0 |
|  | Organic particles | (B-1) | (B-2) | (B-3) | (B-5) | (B-6) | (B-7) | (B-4) | (B-4) | (B-4) | (B-4) |
|  | Particle size (μm) | 0.6 | 2.0 | 3.0 | 10 | 22 | 2.0 | 5.0 | 5.0 | 5.0 | 5.0 |
|  | Formulation amount (mass %) | 10.0 | 10.0 | 10.0 | 10.0 | 10.0 | 10.0 | 10.0 | 10.0 | 0.0 | 10.0 |
|  | Surfactant | (C-1) | (C-1) | (C-1) | (C-1) | (C-1) | (C-1) | (C-2) | (C-3) | (C-4) | (C-5) |
|  | Formulation amount (mass %) | 0.5 | 0.5 | 0.5 | 0.5 | 0.5 | 0.5 | 0.5 | 0.5 | 0.5 | 0.5 |
| Binder | Thermosetting resin | (D-1) | (D-1) | (D-1) | (D-1) | (D-1) | (D-1) | (D-1) | (D-1) | (D-1) | (D-1) |
|  | Formulation amount (mass %) | 5.5 | 5.5 | 5.5 | 5.5 | 5.5 | 5.5 | 5.5 | 5.5 | 5.5 | 5.5 |
| Solvent | Type | NMP | NMP | NMP | NMP | NMP | NMP | NMP | NMP | NMP | NMP |
|  | mass % | 44.0 | 44.0 | 44.0 | 44.0 | 44.0 | 44.0 | 44.0 | 44.0 | 44.0 | 44.0 |
|  | Type | p-Xylene | p-Xylene | p-Xylene | p-Xylene | p-Xylene | p-Xylene | p-Xylene | p-Xylene | p-Xylene | p-Xylene |
|  | mass % | 20.0 | 20.0 | 20.0 | 20.0 | 20.0 | 20.0 | 20.0 | 20.0 | 20.0 | 20.0 |
| Thickness of coating layer (μm) |  | 14 | 16 | 19 | 25 | 31 | 20 | 23 | 20 | 21 | 20 |
| Dispersion stability |  | A | A | A | A | A | A | A | A | A | A |
| Flux resistance |  | A | A. | A | A | A | A | A | A | B | B |
| Wear durability |  | B | A | A | A | B | A | A | A | A | A |

|  |  | Example 21 | Example 22 | Example 23 | Example 24 | Example 25 | Example 26 | Example 27 | Example 28 | Example 29 | Example 30 |
|---|---|---|---|---|---|---|---|---|---|---|---|
| Solid lubricant | Inorganic particles | (A-3) | (A-3) | (A-3) | (A-3) | (A-3) |  | (A-3) | (A-3) | (A-3) | (A-3) |
|  | Particle size (μm) | 1.2 | 1.2 | 1.2 | 1.2 | 1.2 |  | 1.2 | 1.2 | 1.2 | 1.2 |
|  | Formulation amount (mass %) | 20.0 | 20.0 | 20.0 | 30.0 | 10.0 | Not added | 20.0 | 20.0 | 20.0 | 20.0 |
|  | Organic particles | (B-4) | (B-4) | (B-4) |  | (B-4) | (B-4) | (B-4) | (B-4) | (B-4) | (B-4) |
|  | Particle size (μm) | 5.0 | 5.0 | 5.0 |  | 5.0 | 5.0 | 5.0 | 5.0 | 5.0 | 5.0 |
|  | Formulation amount (mass %) | 10.0 | 10.0 | 10.0 | Not added | 20.0 | 30.0 | 0.0 | 10.0 | 10.0 | 10.0 |
|  | Surfactant | (C-6) | (C-1) | (C-1) | (C-1) | (C-1) | (C-1) | (C-1) | (C-1) | (C-1) | (C-1) |
|  | Formulation amount (mass %) | 0.5 | 0.5 | 0.5 | 0.5 | 0.5 | 0.5 | 0.1 | 0.3 | 1.5 | 2.5 |
| Binder | Thermosetting resin | (D-1) | (D-2) | (D-3) | (D-1) | (D-1) | (D-1) | (D-1) | (D-1) | (D-1) | (D-1) |
|  | Formulation amount (mass %) | 5.5 | 5.5 | 5.5 | 5.5 | 5.5 | 5.5 | 5.5 | 5.5 | 5.5 | 5.5 |
| Solvent | Type | NMP | NMP | NMP | NMP | NMP | NMP | NMP | NMP | NMP | NMP |
|  | mass % | 44.0 | 44.0 | 44.0 | 44.0 | 44.0 | 44.0 | 44.4 | 44.2 | 43.0 | 42.0 |
|  | Type | p-Xylene | p-Xylene | p-Xylene | p-Xylene | p-Xylene | p-Xylene | p-Xylene | p-Xylene | p-Xylene | p-Xylene |
|  | mass % | 20.0 | 20.0 | 20.0 | 20.0 | 20.0 | 20.0 | 20.0 | 20.0 | 20.0 | 20.0 |
| Thickness of coating layer (μm) |  | 19 | 20 | 17 | 14 | 24 | 26 | 26 | 23 | 19 | 16 |
| Dispersion stability |  | A | A | A | A | A | A | A | A | A | A |
| Flux resistance |  | B | B | C | A | A | A | B | A | A | A |
| Wear durability |  | A | B | B | B | A | C | A | A | A | B |

TABLE 4

|  |  | Example 31 | Example 32 | Example 33 | Example 34 |
|---|---|---|---|---|---|
| Solid lubricant | Inorganic particles | (A-3) | (A-3) | (A-3) | (A-3) |
|  | Particle size (μm) | 1.2 | 1.2 | 1.2 | 1.2 |
|  | Formulation amount (mass %) | 20.0 | 20.0 | 20.0 | 20.0 |
|  | Organic particles | (B-4) | (B-4) | (B-4) | (B-4) |
|  | Particle size (μm) | 5.0 | 5.0 | 5.0 | 5.0 |
|  | Formulation amount (mass %) | 10.0 | 10.0 | 10.0 | 10.0 |
| Surfactant |  | (C-1) | (C-1) | (C-1) | (C-1) |
| Formulation amount (mass %) |  | 0.5 | 0.5 | 0.5 | 0.5 |
| Binder | Thermosetting resin | (D-1) | (D-1) | (D-1) | (D-1) |
|  | Formulation amount (mass %) | 5.5 | 5.5 | 5.5 | 5.5 |
| Solvent | Type | DMAc | DMF | DMI | HMPA |
|  | mass % | 44.0 | 44.0 | 44.0 | 44.0 |
|  | Type | p-Xylene | p-Xylene | p-Xylene | p-Xylene |
|  | mass % | 20.0 | 20.0 | 20.0 | 20.0 |
| Thickness of coating layer (μm) |  | 20 | 31 | 23 | 19 |
| Dispersion stability |  | A | A | A | A |
| Flux resistance |  | A | A | A | A |
| Wear durability |  | A | A | A | A |

|  |  | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|---|
| Solid lubricant | Inorganic particles |  | (A-3) | (A-3) | (A-3) | (A-3) | (A-3) | (A-3) | (A-3) | (A-3) |
|  | Particle size (μm) |  | 1.2 | 1.2 | 1.2 | 1.2 | 1.2 | 1.2 | 1.2 | 1.2 |
|  | Formulation amount (mass %) | Not added | 20.0 | 20.0 | 20.0 | 20.0 | 20.0 | 20.0 | 20.0 | 20.0 |
|  | Organic particles |  | (B-4) | (B-4) | (B-4) | (B-4) | (B-4) | (B-4) | (B-4) | (B-4) |
|  | Particle size (μm) |  | 5.0 | 5.0 | 5.0 | 5.0 | 5.0 | 5.0 | 5.0 | 5.0 |
|  | Formulation amount (mass %) | Not added | 10.0 | 10.0 | 10.0 | 10.0 | 10.0 | 10.0 | 10.0 | 10.0 |
| Surfactant |  | (C-1) | (C-1) | (C-1) | Not added | (c-7) | (c-8) | (c-9) | (c-10) | (c-11) |
| Formulation amount (mass %) |  | 0.7 | 0.5 | 0.5 |  | 0.5 | 0.5 | 0.5 | 0.5 | 0.5 |
| Binder | Thermosetting resin | (D-1) | (d-4) | (d-5) | (D-1) | (D-1) | (D-1) | (D-1) | (D-1) | (D-1) |
|  | Formulation amount (mass %) | 7.3 | 5.5 | 5.5 | 6.0 | 5.5 | 5.5 | 5.5 | 5.5 | 5.5 |
| Solvent | Type | NMP | NMP | NMP | NMP | NMP | NMP | NMP | NMP | NMP |
|  | mass % | 63.0 | 44.0 | 44.0 | 44.0 | 14.0 | 44.0 | 44.0 | 44.0 | 44.0 |
|  | Type | p-Xylene | p-Xylene | p-Xylene | p-Xylene | p-Xylene | p-Xylene | p-Xylene | p-Xylene | p-Xylene |
|  | mass % | 29.0 | 20.0 | 20.0 | 20.0 | 20.0 | 20.0 | 20.0 | 20.0 | 20.0 |
| Thickness of coating layer (μm) |  | 8 | 20 | 25 | 31 | 21 | 22 | 23 | 22 | Unable to form layer* |
| Dispersion stability |  | — | B | A | C | B | B | C | C | — |
| Flux resistance |  | B | D | D | D | D | D | D | D | — |
| Wear durability |  | D | D | D | C | B | C | B | C | — |

*because of insufficient dispersion stability, spray coating could not be performed.

The raw materials described in Tables above will be described.

Inorganic Particles (A-1):
Molybdenum disulfide particles (manufactured by Daizo Corporation, trade name: "M-5 Powder", particle size: 0.45 μm)

(A-2):
Molybdenum disulfide particles (manufactured by Daizo Corporation, trade name: "A Powder", particle size: 0.63 μm)

(A-3):
Molybdenum disulfide particles (manufactured by Daizo Corporation, trade name: "C Powder", particle size: 1.2 μm)

(A-4):
Molybdenum disulfide particles (manufactured by Daizo Corporation, trade name: "T Powder", particle size: 3.5 μm)

(A-5):
Molybdenum disulfide particles (manufactured by Sumico Lubricant Co., Ltd., trade name: "Moly Powder PA", particle size: 5.2 μm)

(A-6):
Graphite particles (manufactured by Fuji Graphite Works Co., Ltd., trade name: "RCG1Q", particle size: 1.0 μm)

(A-7):
Multi-walled carbon nanotubes (manufactured by Nanocyl SA, trade name: "NC7000", average length (equivalent to particle size): 1.5 μm, average diameter: 9.5 nm)

(A-8):
Boron nitride particles (manufactured by SHOWA DENKO K. K., "SHOBN UHP-S1", particle size: 0.5 μm)

(A-9):
Tungsten disulfide particles (manufactured by Japan Lubricant Co., Ltd., "TUNGMIC A", particle size: 2.0 μm)

(A-10):
Graphite fluoride particles (manufactured by Central Glass Co., Ltd., "CEFBON CMA", particle size: 2.0 μm)

Organic Particles
(B-1):
　Polytetrafluoroethylene particles (manufactured by KITAMURA LIMITED, trade name: "KTL-500F", particle size: 0.6 μm)
(B-2):
　Polytetrafluoroethylene particles (manufactured by KITAMURA LIMITED, trade name: "KTL-1N", particle size: 2.0 μm)
(B-3):
　Polytetrafluoroethylene particles (manufactured by KITAMURA LIMITED, trade name: "KTL-2N", particle size: 3.0 μm)
(B-4):
　Polytetrafluoroethylene particles (manufactured by KITAMURA LIMITED, trade name: "KTL-8N", particle size: 5.0 μm)
(B-5):
　Polytetrafluoroethylene particles (manufactured by KITAMURA LIMITED, trade name: "KTL-IOS", particle size: 10 μm)
(B-6):
　Polytetrafluoroethylene particles (manufactured by KITAMURA LIMITED, trade name: "KTL-450", particle size: 22 μm)
(B-7):
　Melamine isocyanurate particles (manufactured by Nissan Chemical Industries, Ltd., trade name: "MC-6000", particle size: 2.0 μm)
Surfactants
(C-1):
　Fluorine-containing surfactant (manufactured by DIC Corporation, trade name: "MEGAFACE F-444", polyoxyethylene perfluoroalkyl ether)
(C-2):
　Fluorine-containing surfactant (manufactured by 3M Company, trade name: "FLUORAD FC-170C", fluorinated alkylpolyoxyethyleneethanol)
(C-3):
　Fluorine-containing surfactant (manufactured by NEOS COMPANY LIMITED, trade name: "FTERGENT FT-251", α-perfluorononenyloxy-ω-methylpolyethylene oxide)
(C-4):
　Fluorine-containing surfactant (manufactured by DIC Corporation, trade name: "MEGAFACE F-477", copolymer of monomer having fluoroaliphatic group and polyoxyethylene(meth)acrylate)
(C-5):
　Fluorine-containing surfactant (manufactured by DAIKIN INDUSTRIES. LTD., 2-(perfluorohexyl)ethanol)
(C-6):
　Fluorine-containing surfactant (manufactured by DAIKIN INDUSTRIES, LTD., 2-(perfluorohexyl)hexanol)
(c-7):
　Fluorine-free dispersing agent (manufactured by BYK-Chemie GmbH, trade name: "DISPERBYK-111", acidic dispersing agent having phosphate group)
(c-8):
　Fluorine-free dispersing agent (manufactured by Kao Corporation, trade name: "HOMOGENOL L-18", polycarboxylic acid-type acidic dispersing agent)
(c-9):
　Fluorine-free surfactant (manufactured by ADEKA CORPORATION, trade name: "ADEKA HOPE MS-30C", natural alcohol sulfate Na salt)
(c-10):
　Fluorine-free surfactant (manufactured by TAKEMOTO OIL & FAT Co., Ltd., trade name: "PIONIN A-41-B", branched alkylbenzenesulfonic acid Na salt)
(c-11):
　Fluorine-free surfactant (manufactured by Lion Corporation, trade name: "LIPON LH-200", linear alkylbenzenesulfonic acid)
Binder
(D-1):
　Polyamide-imide resin (manufactured by Hitachi Chemical Company. Ltd., trade name: "HPC-6000-26", weight-average molecular weight: 40000, structural unit represented by Formula (1) in which Ar is diphenylmethane structure)
(D-2):
　Polyimide resin (manufactured by UNITIKA LTD., trade name: "U imide AR", the product is polyamic acid and turns into, by a thermal reaction, a polyimide resin)
(D-3):
　Epoxy resin (manufactured by ThreeBond Co., Ltd., trade name: "2237J", one-component type)
(d-4):
　Amorphous polyester (manufactured by TOYOBO CO., LTD., trade name: "VYLON 650", thermoplastic resin)
(d-5):
　Amorphous ester polyurethane (manufactured by TOYOBO CO., LTD., trade name: "UR-1400", thermoplastic resin)
Solvents
　DMAc: N,N-dimethylacetamide
　DMF: N,N-dimethylformamide
　DMI: 1,3-dimethyl-2-imidazolidinone
　HMPA: hexamethylphosphoric triamide
　As described in Tables above, in the case of a coating composition not containing a solid lubricant, so that the coating layer formed from this coating composition and on the surface of a wire did not have a solid lubricant, this wire was found to have poor wear durability Comparative Example 1

In the case of a coating composition containing, as the binder, a thermoplastic resin, so that the coating layer formed from this coating composition and on the surface of a wire had, as the binder, the thermoplastic resin, both characteristics of flux resistance and wear durability were found to be poor (Comparative Examples 2 and 3).
　In the case of a coating composition not containing a fluorine-containing surfactant, so that the coating layer formed from this coating composition and on the surface of a wire did not contain a fluorine-containing surfactant, even in the case of containing ordinary fluorine-free dispersing agent and surfactant, flux resistance was found to be very poor (Comparative Examples 4 to 8). Note that, in the case of using, as the surfactant, the linear alkylbenzenesulfonic acid, dispersion stability was found to be markedly poor, and uniform spray coating could not be performed (Comparative Example 9).
　By contrast, wires on the surfaces of which coating layers were formed from coating compositions satisfying features of the present invention were all excellent in both characteristics of flux resistance and wear durability (Examples 1 to 34). In addition, the coating compositions of Examples 1 to 34 all exhibited high dispersion stability.
　The present invention has been described together with embodiments thereof; however, we do not intend to limit our invention in any minor portion of the descriptions unless otherwise specified; we believe that the invention is construed broadly without departing from the spirit and scope of the invention described in the attached claims.

REFERENCE SIGNS LIST 2 electronic endoscope (endoscope)
3 insertion part
3a flexible tube
3b bending part (angle part)
3c tip part
5 main-body operating unit
6 universal cord
11 force gage
12 lubricating wire
13, 15 pulleys
16 weight
A stroke (10 mm)
α angle (100°)

What is claimed is:

1. An endoscopic coating composition comprising a solid lubricant, a fluorine-containing surfactant, a thermosetting resin, and a solvent,
wherein the fluorine-containing surfactant includes a fluorine-containing surfactant having at least one moiety of an alcoholic hydroxy group, a polyether structure, or a (meth)acrylate monomer-derived component.

2. The endoscopic coating composition according to claim 1, wherein the fluorine-containing surfactant includes a nonionic fluorine-containing surfactant.

3. The endoscopic coating composition according to claim 1, wherein the fluorine-containing surfactant includes a fluorine-containing surfactant having a polyoxyalkylene structure.

4. The endoscopic coating composition according to claim 1, wherein the solvent includes at least one of N-methyl 2-pyrrolidone, xylene, N,N-dimethylacetamide, N,N-dimethylformamide, hexamethylphosphoric triamide, or 1,3-dimethyl-2-imidazolidinone.

5. The endoscopic coating composition according to claim 1, wherein the thermosetting resin includes a polyamide-imide resin.

6. The endoscopic coating composition according to claim 5, wherein the polyamide-imide resin includes, as a polyamide-imide constituent component, a structural unit represented by Formula (1) below:

Formula (1)

where Ar represents a divalent group having an aromatic ring.

7. The endoscopic coating composition according to claim 6, wherein Ar in Formula (1) above represents phenylene, a diphenylmethane structure, a diphenylpropane structure, a diphenyl ether structure, a diphenyl sulfone structure, a diphenylamine structure, a biphenyl structure, or a naphthalene structure.

8. The endoscopic coating composition according to claim 7, wherein Ar in Formula (1) above represents phenylene, a diphenylmethane structure, a diphenylpropane structure, a diphenyl ether structure, or a diphenylamine structure.

9. The endoscopic coating composition according to claim 5, wherein the polyamide-imide resin has a weight-average molecular weight of 10000 to 100000.

10. The endoscopic coating composition according to claim 1, wherein the solid lubricant includes inorganic particles, and the inorganic particles include at least one of graphite, graphite fluoride, carbon nanotubes, boron nitride, molybdenum disulfide, organic molybdenum, or tungsten disulfide.

11. The endoscopic coating composition according to claim 10, wherein the inorganic particles have a particle size of 0.2 to 4.0 μm.

12. The endoscopic coating composition according to claim 11, wherein the inorganic particles have a particle size of 0.3 to 1.5 μm.

13. The endoscopic coating composition according to claim 1, wherein the solid lubricant includes organic particles, and the organic particles include at least one of a fluororesin or melamine cyanurate.

14. The endoscopic coating composition according to claim 13, wherein the organic particles have a particle size of 0.5 to 30 μm.

15. The endoscopic coating composition according to claim 14, wherein the organic particles have a particle size of 1 to 15 μm.

16. An endoscopic lubricating member provided by a coating treatment using the endoscopic coating composition according to claim 1.

17. The endoscopic lubricating member according to claim 16, wherein the endoscopic lubricating member is an endoscopic lubricating wire.

18. A method for producing an endoscopic lubricating member, the method comprising coating a surface of an endoscopic member with the endoscopic coating composition according to claim 1.

19. An endoscopic flexible tube comprising the endoscopic lubricating member according to claim 16.

20. An endoscope comprising the endoscopic flexible tube according to claim 19.

* * * * *